United States Patent [19]
Kiel et al.

[11] Patent Number: 5,856,108
[45] Date of Patent: Jan. 5, 1999

[54] BIOSYNTHESIS OF DIAZOMELANIN AND DIAZOLUMINOMELANIN AND METHODS THEREOF

[75] Inventors: Johnathan L. Kiel; Jill E. Parker; Eric A. Holwitt; Harvey A. Schwertner, all of San Antonio, Tex.

[73] Assignee: The United States of America as represented by the Secretary of the Air Force, Washington, D.C.

[21] Appl. No.: 779,694

[22] Filed: Oct. 21, 1991

[51] Int. Cl.$^6$ ............... C12Q 1/00; C12Q 1/04; C12Q 1/26
[52] U.S. Cl. .......... 435/7.32; 435/7.37; 435/7.72; 435/29; 435/34; 435/41
[58] Field of Search ................. 435/7.32, 7.37, 435/7.72, 25, 29, 34, 69.1, 41, 106, 108

[56] References Cited

U.S. PATENT DOCUMENTS

| | | | |
|---|---|---|---|
| 4,283,490 | 8/1981 | Plakas et al. | 435/8 |
| 5,003,050 | 3/1991 | Kiel et al. | 534/573 |
| 5,089,395 | 2/1992 | Snyder et al. | 435/39 |

OTHER PUBLICATIONS

"Melanin Production. . . ", della–Croppa et al. Biotechnology, vol. 8, Jul. 1990, pp. 634–638.
"Isolation and Characterization. . . ", Fernandez et al. Proc. Natl. Acad. Sci. USA, vol. 86, Sep. 1989, pp. 6449–6453.
"Biochemical and Immonological. . . ", Iobbi et al. EOR. J. Biochem, 168, 451–459 (1987).
"Stable Nuclear. . . ", Kindle et al. J. Cell Biology, vol. 109, 2589–2601 (1989).
Kiel et al, "interactions of the antioxidants 3–amino–L–tyrosine and diazoluminomelanin with cytochrome b of HL–60 cells", Free Radical Biol. Med. 9(supp.1) : 15. (1990).
Chaudhry et al., "Cytochrome b from *E Scherichia coli* Nitrate Reductase,"JBC, 258 (9):5819–5827. (1983).

*Primary Examiner*—John L. LeGuyader
*Attorney, Agent, or Firm*—Charles E. Bricker; Thomas L. Kundert

[57] ABSTRACT

There is provided a method for producing diazoluminomelanin (DALM) which comprises culturing in a medium containing nitrate, 3-amino-L-tyrosine (3-AT) and luminol under suitable metabolic conditions, a microorganism containing nitrate reductase.

Also provided is a method for directly detecting microorganisms containing nitrate reductase or those into which nitrate reductase can be introduced by recombinant DNA technology, which comprises culturing the microorganism in a medium containing nitrate, 3-amino-L-tyrosine (3-AT) and luminol under suitable metabolic conditions, transferring the medium to a microtiter plate or tube coated with antibody or an antiligand to which the microorganism would specifically bind, washing the plate or tube and activating luminescence.

Further, there is provided a method for producing diazomelanin (DM) which comprises culturing in a medium containing nitrate and 3-amino-L-tyrosine (3-AT) under suitable metabolic conditions, a microorganism containing nitrate reductase.

Yet further, there is provided a method for directly detecting microorganisms containing nitrate reductase or those into which nitrate reductase can be introduced by recombinant DNA technology, which comprises culturing the microorganism in a medium containing nitrate and 3-amino-L-tyrosine (3-AT) under suitable metabolic conditions, transferring the medium to a microtiter plate or tube coated with antibody or an antiligand to which the microorganism would specifically bind, washing the plate or tube, adding luminol and activating luminescence.

12 Claims, 1 Drawing Sheet

BIOSYNTHESIS OF DIAZOMELANIN AND DIAZOLUMINOMELANIN AND METHODS THEREOF

RIGHTS OF THE GOVERNMENT

The invention described herein may be manufactured and used by or for the Government of the United States for all governmental purposes without the payment of any royalty.

BACKGROUND OF THE INVENTION

This invention relates to luminescent reagents.

Specific binding assays provide an economical means for detecting and measuring an analyte present in low-concentrations in a sample. Specific binding assays are based upon the interaction of two bindable substances, one the analyte and the other a specific binding partner, which specifically recognize each other. Examples of specific binding partners whose interaction can serve as the basis for a specific binding assay include antigens-antibodies, biotin-avidin, nucleic acid probes, enzymes-substrates, enzymes-inhibitors, enzymes-cofactors, chelators-chelates, and cell surface receptor pairs. Assays involving other specifically bindable substances are also known and within the scope of the present invention. Specific binding assays have shown great utility in determining various analytes in biological, medical, environmental, agriculture and industrial applications.

A variety of assays using the principles of the specific binding approach are known, and several have become important diagnostic tools. In one such type of specific binding assay, the immunoassay, the analyte is an antibody, antigen, or hapten, and is made to react with another member of this group. While the background discussion will focus on such immunoassays, this focus is made for clarity of presentation, and is not to be interpreted as limiting of the invention.

A variety of labelling reactions have been proposed for use in specific binding assays, including radioactive, enzymatic, chromogenic and luminogenic procedures. In a radioactive labelling procedure, the component conjugated with the specific binding partner is an atom or molecule which emits radioactivity. Chromogenic and luminogenic labelling reactions are chemically more complex, in that several reactants may be involved. The chromophore or lumiphore may itself be the label in the reaction, or a catalyst, typically an enzyme, may be used as the label. When the catalyst is used as the label, it will react with catalytic substrates which in turn produce color or luminescence. The remaining components of the reaction, that is, those not conjugated to the binding partner, are supplied in a chromogenic or luminogenic reagent medium, so that the uniting of the labelled conjugate and the reagent medium results in the desired color change or light emission, respectively.

Luminescent labels are attractive alternatives for use in specific binding assays for a variety of reasons. Luminescence is broadly defined as the production of visible light by atoms that have been excited by the energy produced in a chemical reaction, usually without an associated production of heat. Chemical energy excites electrons in the light-emitting molecules to higher energy states, from which electrons eventually fall to lower energy states with the emission of quanta of energy in the form of visible light. Luminescence is observed in several synthetic chemical compounds and also in naturally occurring biological compounds such as found in fireflies and certain varieties of fish.

One of the most important families of chemiluminescent molecules are the phthalylhydrazides. The most familiar member of this family is luminol, or 5-amino-2,3-dihydro-1,4-phthalazinedione, which has a gross chemical composition of $C_8H_7N_3O_2$ and a double ring structure with a melting point of about 320° C. Luminol is commercially available from several suppliers and is well characterized. Certain luminol analogs are also chemiluminescent, such as those wherein the position of the amino group is shifted (e.g., isoluminol, the amino group being at the 6 position), or is replaced by other substituents, as well as annelated derivatives and those with substitution in the nonheterocyclic ring. Some luminol analogs produce light more efficiently than does luminol itself, while others have lower efficiency. (As used herein, the term "luminol" encompasses such related species.)

Generally, luminol produces light in an oxidizing reaction, wherein the luminol combines with oxygen or an oxidizer to produce a reaction product and photons at a wavelength of about 425–450 nanometers (nm). The precise reaction formula and the quantum efficiency of light production, i.e., the ratio of luminescing molecules to total molecules of the luminescent species, depend upon the medium in which the luminol resides, temperature and other reaction conditions. Typical oxidizers used in conjunction with luminol include oxygen, hydrogen peroxide, hypochlorite, iodine and permanganate.

The oxidation of luminol with the associated production of light occurs rather slowly at ambient temperatures, unless the reaction is catalyzed. A variety of different substances can catalyze the reaction, including organic enzymes, e.g., horseradish peroxidase, other organic molecules such as microperoxidase and heme, positive metallic ions such as the cupric ion, and negative ions such as the ferricyanate ion.

Luminescent molecules would appear to be highly desirable as tags in specific binding assays because of their stability, sensitivity, the potential ease of detecting their emitted visible light and their lack of toxicity. Commercial luminol, however, has proven to be unsuitable for such purposes. There exists a need for specific improvements in the light emission characteristics of the reaction for use with such assays. Heretofore, commercial luminol has not shown sufficient activity to be useful to measure analytes at low concentrations in specific binding assays. The light emission intensity of the luminol reaction may be sufficient where high concentrations of catalyst are employed and where highly sophisticated and sensitive photometers are available, but the luminescent intensity has not been sufficient with low concentrations of catalyst and where other detection media such as photographic film or less sensitive photometers are used.

While the luminol reaction therefore offers important potential benefits in the measurement of the presence and amount of a reaction component, for many potential applications, the intensity of the emitted light is too low. Further, the light emitted from commercial luminol exhibits an early flash of light within the first few seconds of the initiation of the reaction, followed by a progressive and rapid decrease in light emission over time. The integrated light intensity during any fixed period of time is therefore likely to be different from that measured over any other equal period of time. This variability may result in irreproducibility between tests. Desirably, there would be some period of time during which the light emission from the luminol reaction is relatively constant, so that the measurement of integrated light intensity could begin at different times after initiation of the reaction, but within the period of constant light output, without variability of the results. This would eliminate the requirement that the reagents be added to a solution fixed in front of the luminescence detector which puts severe constraints on the light measuring system.

Higgins et al, U.S. Pat. No. 4,743,541, disclose that the intensity and duration of emitted light from luminol can be considerably improved by repeatedly dissolving and recrystallizing the luminol until sulphide and hydrazine levels are below about 100 ppm.

The production of chemiluminescence with luminol comprises dissolving the luminol in an organic solvent, such as DMSO or acetone, or in a strong base and diluting the solution in a buffer of desired pH. The amount of luminol that can be dissolved is severely limited by the relative insolubility of luminol in water at a pH below 10.

When luminol is covalently attached to carriers such as protein, its chemiluminescence is quenched. Isoluminol, although less efficient in light production than luminol, is quenched to a lesser degree by covalent attachment. The noncovalent attachment of luminol to bovine serum albumin prevents quenching and solubility problems, but "leaks" luminol into the solution by forming an equilibrium between bound and unbound luminol, thus decreasing the specificity of luminol/carrier dependent immunoassays and enzyme-linked assays.

There is a need for a luminescent probe which is water soluble, is highly quantum efficient, and provides long-lived chemiluminescence.

U.S. Pat. No. 5,003,050, issued Mar. 26, 1991, to Johnathan L. Kiel and Gerald J. O'Brien, discloses a water-soluble luminescent compound having repeating units of the formula:

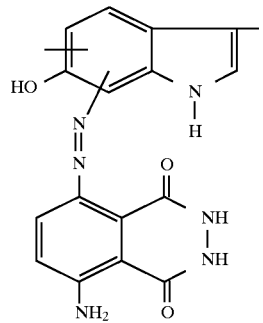

The product, which is a polymer having repeating units comprising diazo-linked luminol and hydroxyindole, is referred to as diazoluminomelanin (DALM), since one of the precursors to this product, 3-amino-L-tyrosine (3AT) is closely related to the biological substrates which are converted into melanin.

DALM is water soluble, having an apparent pKa for solubility about pH 5.0. DALM does not require a catalyst for chemiluminescence. The duration of the reaction is in excess of 52 hours. In contrast, luminol requires a catalyst; with microperoxidase as the catalyst, luminol has shown peak luminescence at 1 sec and half-lives of light emission of 0.5 and 4.5 sec at pH 8.6 and 12.6, respectively. The chemiluminescence yield of DALM is better at pH 7.4 than at pH 9.5, although it still provides a strong signal at strongly basic pHs. DALM also produces chemiluminescence at pH 6.5 which is about the same intensity as that produced at pH 9.5.

DALM can be used for chemiluminescent immunoassays for biological and chemical agents; in radiofrequency and ionizing radiation dosimeters; and for RNA/DNA hybridization assays for viruses and genetic detection.

Also disclosed in U.S. Pat. No. 5,003,050 is a method for preparing DALM which comprises reacting 3AT with an alkali metal nitrite, and reacting the resulting diazonium salt with luminol. The method involves the use of organic solvents such as dimethylsulfoxide and acetone. On a large scale, handling and disposal of such solvents could be both dangerous and difficult.

Accordingly, it is an object of the present invention to provide a biosynthetic method for producing DALM.

Other objects, aspects and advantages of the present invention will be apparent to those skilled in the art from a reading of the following detailed disclosure of the invention.

SUMMARY OF THE INVENTION

In accordance with the present invention there is provided a method for producing diazoluminomelanin (DALM) which comprises culturing in a medium containing nitrate, 3-amino-L-tyrosine (3-AT) and luminol under suitable metabolic conditions, a microorganism containing nitrate reductase.

Also provided in accordance with the invention is a method for directly detecting microorganisms containing nitrate reductase or those into which nitrate reductase can be introduced by recombinant DNA technology, which comprises culturing the microorganism in a medium containing nitrate, 3-amino-L-tyrosine (3-AT) and luminol under suitable metabolic conditions, transferring the medium to a microtiter plate or tube coated with antibody or an antiligand to which the microorganism would specifically bind, washing the plate or tube and activating luminescence.

Further, in accordance with the present invention there is provided a method for producing diazomelanin (DM) which comprises culturing in a medium containing nitrate and 3-amino-L-tyrosine (3-AT) under suitable metabolic conditions, a microorganism containing nitrate reductase.

Yet further, there is provided a method for directly detecting microorganisms containing nitrate reductase or those into which nitrate reductase can be introduced by recombinant DNA technology, which comprises culturing the microorganism in a medium containing nitrate and 3-amino-L-tyrosine (3-AT) under suitable metabolic conditions, transferring the medium to a microtiter plate or tube coated with antibody or an antiligand to which the microorganism would specifically bind, washing the plate or tube, adding luminol and activating luminescence.

DETAILED DESCRIPTION OF THE INVENTION

Figure 1:
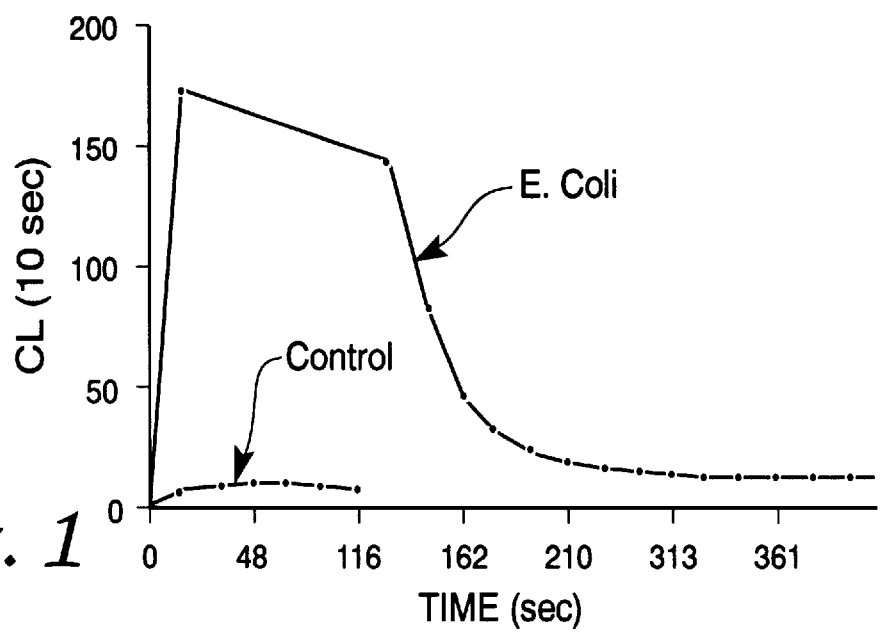
FIG. 1 illustrates the luminescent response of diazomelanin produced by E. coli.

The microorganisms which may be employed in accordance with the invention include all organisms containing nitrate reductase, i.e., those inherently containing nitrate reductase and those into which nitrate reductase can be introduced by recombinant DNA technology. Nitrate reductase is found in several strains of Escherichia coli (E. coli), salmonella, fungi such as, for example, Neurospora crassa, algae such as, for example, Chlamydomonas reinhardtii, denitrifying bacteria such as, for example, *Micrococcus denitrificans,* and higher plants. The gene for nitrate reductase has been cloned and can be transferred in expression vectors such a plasmids and bacteriophages.

The culture medium must be suitable for the microorganism employed. Nitrate, 3-AT and, optionally, luminol, as noted previously, are added to the medium. 3-AT exhibits bacteriostatic properties; accordingly, it may be necessary to carry out some experimentation to determine the maximum and desired levels of 3-AT.

The conditions for culturing the microorganisms will vary depending upon the microorganism under investigation. For example, we found that certain strains of *E. coli* without tyrosinase require nitrate reducing conditions followed by aerobic conditions, while other microorganisms produced DALM under aerobic conditions. In the first case, the microorganisms are grown under anaerobic to microaerophillic conditions to optimize production of nitrite and, subsequently, diazotyrosine. The medium is then oxygenated to facilitate conversion of diazotyrosine to diazomelanin (DM). When luminol is present, the same procedure is followed yielding diazotyrosine and diazoluminol which react to form diazoluminomelanin.

Activation of DM and DALM is accomplished by mixing the culture with a suitable base and hydrogen peroxide and reading the resulting luminescence.

Diazomelanin (DM) and diazoluminomelanin (DALM) can be used in producing thermochemiluminescent radiofrequency radiation microdosimeters. They can also be used as ultraviolet light absorbers, microwave and radiofrequency radiation absorbers, cation exchangers, bioelectrodes, semiconductors and drug-binding biopolymers. In addition, when DM and DALM are produced intracellularly, they can link by diazocoupling and alkylation to nucleic acids and proteins produced by the microorganisms. Transferred nucleic acids and proteins from cloned genes can be produced and labeled with the luminescent polymers in the microorganisms as part of the same process. These labeled products can then be recovered and purified for their ultimate use as diagnostic probes and therapeutic agents. Examples of labeled proteins include immunoglobulins, enzymes, receptor proteins, nucleic acid binding proteins, and specific protein binding proteins. Such labeled probes may be used therapeutically to target unwanted genetic material, viral genomes and whole viruses, pathogenic bacteria, fungi, protozoans, parasites and tumor cells for destruction by free radical reactions and heating by microwave and radiofrequency radiation absorption mediated by the DM or DALM.

The processes of this invention do not require dangerous and difficult to handle organic solvents. These processes can be operated on a large scale with a nonpathogenic bacteria. In situ labeling of nucleic acids and proteins can be accomplished without further organic chemical manipulation. Unlike other immunoassay or ligand-antiligand tests, dead organisms are not detected since only metabolizing organisms can produce DM or DALM.

The following examples illustrate the invention:

EXAMPLE I

Four strains of *E. coli*, HB101, LE392, C600 and MC1061, were tested on agar slants containing yeast extract (3 g/l), tryptone (5 g/l), potassium nitrate (1 g/l), agar (12 g/l) and 3-AT (0.2, 0.3 and 0.4 mM). After 48 h of incubation at 37° C., HB101 showed growth but no browning of medium containing 0.2 mM 3-AT. LE392 and C600 showed growth and browning of the inoculated slant. None of the strains showed growth with 0.4 mM 3-AT at 48 h. At 72 h, the results were the same for the respective strains at 0.2 mM 3-AT, except that LE392 showed darkening of the colonies. C600 was the only strain that displayed growth (only on the surface of the slant) at 0.4 mM 3-AT at 72 h with browning of the medium. The growth and diazomelanin production by *E. coli* in nitrate/3-AT agar slants under aerobic conditions is given in Table I, below.

TABLE I

| Strain | 3-AT(mM) | Culture Time (hours) | | |
|---|---|---|---|---|
| | | 48 | 72 | 120 |
| HB101 | 0.2 | G | G | G + B |
| | 0.4 | NG | NG | NG |
| LE392 | 0.2 | G + B | G + B | G + B |
| | 0.4 | NG | NG | NG |
| C600 | 0.2 | G + B | G + B | G + B |
| | 0.4 | NG | G + B | G + B |
| CONTROL | 0.2 | NG | NG | NG |
| | 0.4 | NG | NG | NG |

Key: G = Growth, B = Browning, NG = No Growth

The growth and diazomelanin production by *E. coli* in nitrate/3-AT agar slants under microaerophilic followed by aerobic conditions is given in Table II, below.

TABLE II

| STRAIN | 3-AT(mM) | Culture Time (days) | |
|---|---|---|---|
| | | Microaerophilic (5) | Aerobic (3) |
| LE392 | 0.2 | G + B | G + B + C |
| | 0.3 | G | G + B |
| C600 | 0.2 | G | G + B |
| | 0.3 | NG | NG |
| MC1061 | 0.2 | G | G + B |
| | 0.3 | T | T + B |
| CONTROL | 0.2 | NG | NG |
| | 0.3 | NG | NG |

Key: G = Growth, B = Browning, NG = No Growth C = Pigmented Colonies, T = Surface Growth These data illustrate that *E. coli* can be used to produce diazomelanin, although the process is strain-restricted and limited by the bacteriostatic property of 3-AT.

EXAMPLE II

Medium containing diazomelanin was tested for luminescence by adding 900 μl of 3% $H_2O_2$ and 100 μl concentrated NaOH to approximately 10 mg of agar containing the pigment. Luminescence was recorded in a Turner 20e luminometer. The results are shown, compared to uncultured medium, in FIG. 1.

EXAMPLE III

Figure 2:
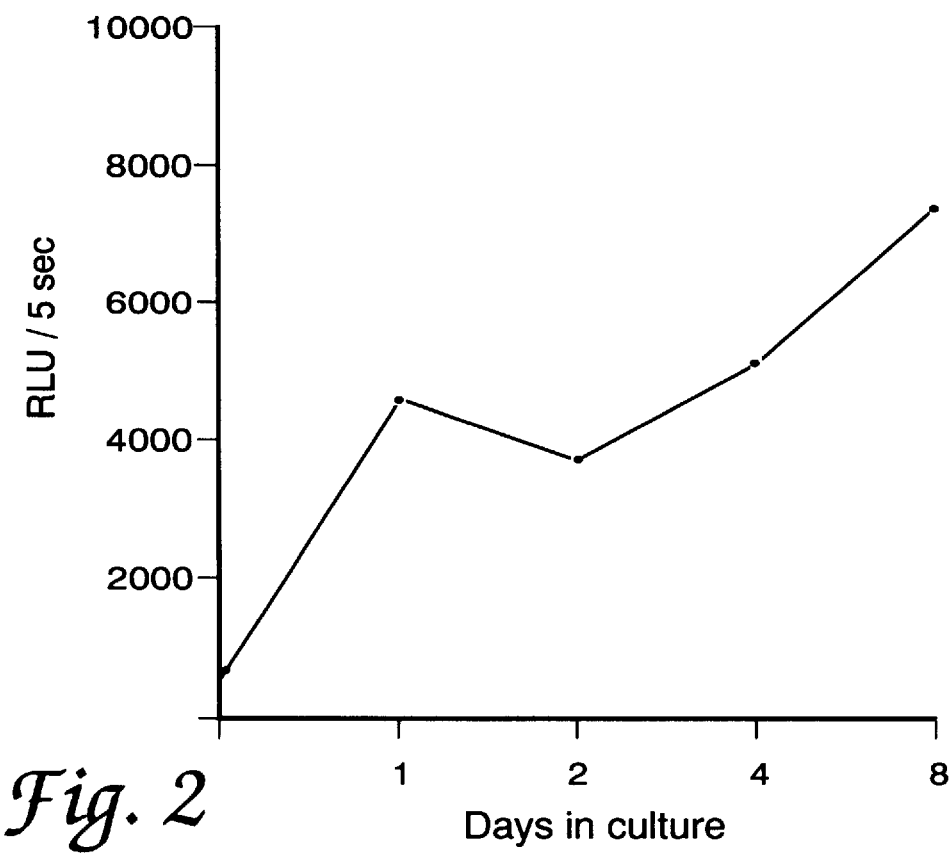
FIG. 2 illustrates the luminescent response of diazoluminomelanin produced by Bacillus Cereus at 1, 2, 4 and 8 days.

Bacillus Cereus was cultured in a nutrient broth containing 12 g $KNO_3$, 100 mg luminol and 80 mg 3-AT. 20 μl of supernatant was removed from the cultures at 1, 2, 4 and 8 day intervals. The supernatant was added to 250 μl deionized water, 50 μl 0.3M $Na_2CO_3$ and 50 μl 0.3% $H_2O_2$ and heated to 45° C. Luminescence was integrated for 5 seconds in a Turner 20e luminometer. The results are shown in FIG. 2.

Various modifications of the present invention can be made in view of the foregoing disclosure without departing from the spirit and scope of the invention.

We claim:

1. A method for producing diazoluminomelanin (DALM) which comprises culturing a microorganism containing nitrate reductase in a medium containing nitrate, 3-amino-L-tyrosine (3-AT) and luminol under suitable metabolic conditions.

2. The method of claim 1 wherein said microorganism does not contain tyrosinase, wherein said metabolic conditions comprise nitrate reducing conditions followed by aerobic conditions.

3. The method of claim 1 wherein said microorganism contains tyrosinase, wherein said metabolic conditions comprise aerobic conditions.

4. A method for detecting microorganisms containing nitrate reductase, which comprises culturing the microorganism in a medium containing nitrate, 3-amino-L-tyrosine (3-AT) and luminol under suitable metabolic conditions, transferring the medium to a microtiter plate or tube coated with antibody or an antiligand to which the microorganism would specifically bind, washing the plate or tube and activating luminescence.

5. The method of claim 4 wherein said microorganism does not contain tyrosinase, wherein said metabolic conditions comprise nitrate reducing conditions followed by aerobic conditions.

6. The method of claim 4 wherein said microorganism contains tyrosinase, wherein said metabolic conditions comprise aerobic conditions.

7. A method for producing diazomelanin (DM) which comprises culturing a microorganism containing nitrate reductase in a medium containing nitrate and 3-amino-L-tyrosine (3-AT) under suitable metabolic conditions.

8. The method of claim 7 wherein said microorganism does not contain tyrosinase, wherein said metabolic conditions comprise nitrate reducing conditions followed by aerobic conditions.

9. The method of claim 7 wherein said microorganism contains tyrosinase, wherein said metabolic conditions comprise aerobic conditions.

10. A method for detecting microorganisms containing nitrate reductase, which comprises culturing the microorganism in a medium containing nitrate and 3-amino-L-tyrosine (3-AT) under suitable metabolic conditions, transferring the medium to a microtiter plate or tube coated with antibody or an antiligand to which the microorganism would specifically bind, washing the plate or tube, adding luminol and activating luminescence.

11. The method of claim 10 wherein said microorganism does not contain tyrosinase, wherein said metabolic conditions comprise nitrate reducing conditions followed by aerobic conditions.

12. The method of claim 10 wherein said microorganism contains tyrosinase, wherein said metabolic conditions comprise aerobic conditions.

* * * * *